United States Patent [19]

Koudsi et al.

[11] Patent Number: 5,648,331

[45] Date of Patent: Jul. 15, 1997

[54] METHOD OF INHIBITING TISSUE ISCHEMIA AND REPERFUSION INJURY

[75] Inventors: Basem Koudsi; Tze-Chein Wun, both of St. Louis, Mo.

[73] Assignee: G.D. Searle & Co., Chicago, Ill.

[21] Appl. No.: 297,196

[22] Filed: Aug. 26, 1994

[51] Int. Cl.$^6$ .............................. C12N 7/00; C12N 9/00
[52] U.S. Cl. .............................. 514/12; 514/8; 514/21
[58] Field of Search .............................. 514/8, 12, 21

[56] References Cited

U.S. PATENT DOCUMENTS 5,276,015  1/1994  Khouri et al. .............................. 514/12

*Primary Examiner*—Elizabeth C. Weimar
*Assistant Examiner*—Patricia Touzeau
*Attorney, Agent, or Firm*—Dennis A. Bennett

[57] ABSTRACT

A method for reducing the extent of tissue ischemia and reperfusion injury in a warm-blooded mammal is disclosed which comprises administering by local, regional, or systemic perfusion to the site of a bodily injury subject to interval tissue ischemia in said mammal a small but effective amount of tissue factor pathway inhibitor (TFPI) sufficient to reduce the extent of said tissue ischemia and reperfusion injury.

13 Claims, 6 Drawing Sheets

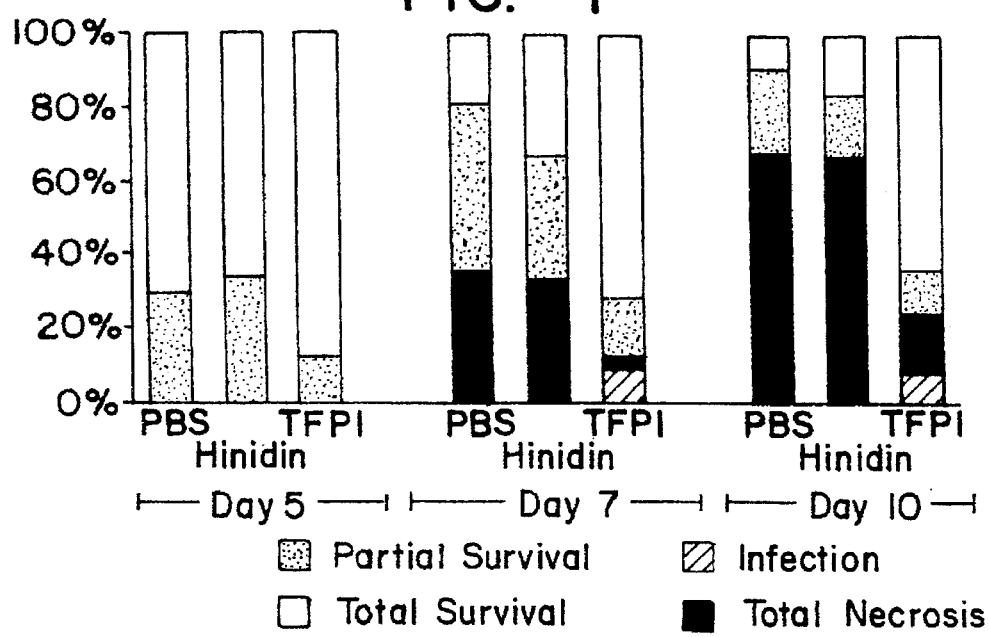
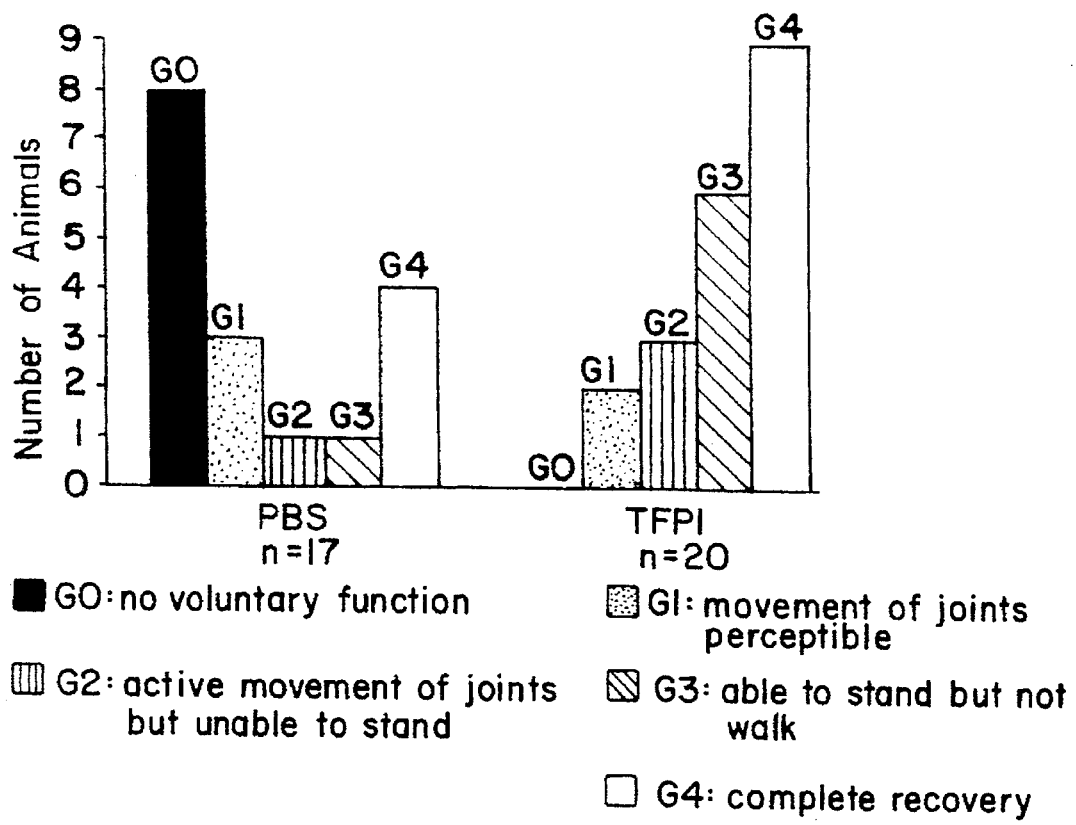

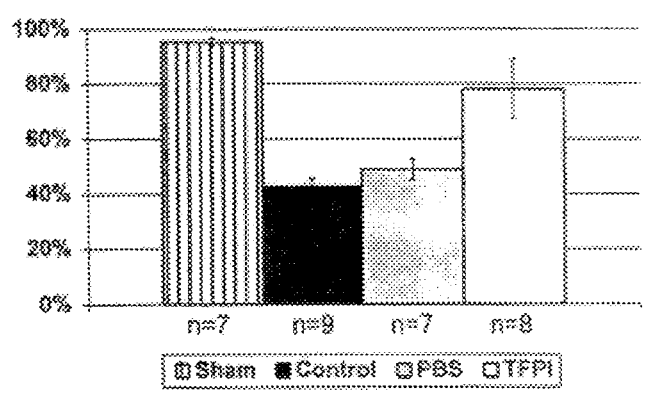
Figure 5: Percent muscle survival after 3.5 hours of ischemia.

METHOD OF INHIBITING TISSUE ISCHEMIA AND REPERFUSION INJURY

BACKGROUND OF THE INVENTION

This invention relates to a novel method for inhibiting tissue ischemia and reperfusion injury and, more particularly, to a method of reducing the extent of tissue injury in the clinical setting of crush injury, amputation, organ transplantation, cerebral vascular diseases (e.g. stroke), ischemic heart diseases (e.g. myocardial infarction), peripheral vascular diseases, and similar such injuries.

Reperfusion injury refers to the cellular changes and tissue damage seen after a period of total ischemia followed by reperfusion. Extremity replantation, organ transplantation, free flap tissue reconstruction and even myocardial infarction and stroke are all clinical examples of interval tissue ischemia which can lead to tissue loss due to reperfusion injury after blood flow is reestablished. Tissue reperfusion injury, seen in its full clinical extent as the no-reflow phenomenon, appears as an inflammatory response to reperfusion resulting in the ultimate death of the tissue.

The tissue injury that occurs after a period of total ischemia and subsequent revascularization (reperfusion injury) has several proposed coincident mechanisms that often lead to either partial or complete tissue necrosis. The extent of injury primarily depends upon the length of time and degree of ischemia as well as the type of tissues affected. The pathology of the observed tissue injury includes vascular and cellular responses [Peacock, in *Wound Repair*, (E. E. Peacock, ed.) Saunders, Philadelphia, p. 1 (1984); and Davis and Allison, in *Handbook of Experimental Pharmacology*, (J. R. Vane and S. H. Ferreira, eds.) Springer, N.Y., p. 267 (1978)]:

a) The vascular response involves an increased vessel wall permeability to plasma and macromolecules, which is responsible for the edema formation;

b) The cellular response is characterized by the appearance of neutrophils;

c) Lysosomal enzymes and other mediators, such as eicosanoides, released from these cells after specific stimuli or cell death may contribute to tissue damage and necrosis; and d) Intravascular thrombosis.

In the clinical setting, while the tissue injury caused by the period of anoxia may be fixed and irreversible, further tissue injury by the circulating blood cells, intravascular thrombosis and tissue edema may be preventable. A multitude of agents have been studied and reported heretofore with varying degrees of limited success. No one agent has been demonstrated to have superior effects such that it has moved into common clinical usage.

The mechanism of reperfusion injury is highly complex and remains only partially understood. It is believed that xanthine dehydrogenase is converted to xanthine oxidases within the endothelial cell during ischemia, permitting the production of superoxide ($O_2-$) which causes the initial endothelial cell injury. Secondarily, the superoxide may activate neutrophils which act as an amplifier of the initial injury [Sussman and Bulkley, *Methods Enzymol.* 186, 711–723 (1990)]. In response to endothelial/vascular injury, multiple cellular and humoral activations occur that mediate a host of hemostatic and inflammatory processes. During the hemostatic process, a number of products are generated which are proinflammatory. For example, the product of the coagulation cascade, thrombin, has been shown to activate cells involved in the inflammatory process, such as endothelial cells, platelets, neutrophils, monocytes and smooth muscle cells [M. A. Shuman, *Ann. NY Acad. Sci.* 485, 228–239 (1985); and Carney et al., *Sem. Thromb. Hemost.* 18, 91–103 (1992)]. Further evidence that coagulation is closely linked to inflammation has recently been reviewed by Esmon et al., *Thromb. Haemost.* 66 160–165, (1991). The expression of tissue factor on the damaged endothelium and activated monocyte/macrophages is thought to initiate the coagulation cascade [Nemerson, *Sem. Hematol.* 29, 170–176 (1992); and Rapaport and Rao, *Arteriosclerosis Thromb.* 12, 1111–1121 (1992)] and this expression has been shown to be greatly enhanced under inflammatory conditions [Edwards and Rickles, *Sem. Hematol.* 29, 202–212 (1992)]. These considerations suggest that connection between coagulation and inflammation occurs during vascular injury, and inhibition of the tissue factor activity in the injured vessels may lead to modulation of inflammatory response.

A large body of work heretofore has focused especially on the role of leukocytes (neutrophils in particular) and oxygen-derived free radicals in ischemia injury. Using a cat small intestine model, it was shown that anti-neutrophil serum or monoclonal antibody that inhibits neutrophil adherence to endothelial cells prevented reperfusion-induced capillary leak [Hernandez et al., *Am. J. Physiol.* 253, H699–703 (1987)]. In many other models it was shown that scavengers of oxygen metabolites (e.g. superoxide dismutase, catalase, dimethyl sulfoxide), chelators of iron (e.g. desferrioxamine, transferrin), and inhibitors of xanthine oxidase (e.g. allopurinol, pterin aidehyde, tungsten feeding) provided protection from ischemia/reperfusion injury [Sussman and Bulkley, *Methods Enzymol.* 186, 711–723 (1990)]. However, oxygen-free radical scavengers have not always been reported to be beneficial in all systems studied and they do not prevent all of the injury patterns noted [Winchell and Halasz, *Transplantation* 48, 393–396 (1989)]. Steroids and other synthetic compounds that exert their anti-inflammatory action by reducing the availability of arachidonic acid for conversion to prostaglandins and leukotrienes were found to inhibit the progression of necrosis in an ischemic rabbit ear model [Hayden et al., *Prostaglandins* 33, 63–73 (1987)]. Use of anti-thrombotic agents has also reportedly shown improved results after reperfusion. For example, streptokinase and urokinase have been shown to improve the rat epigastric flap [Jacobs et al., *Plast. Reconstr. Surg.* 68,737 (1981)] and replanted limbs [Zdeblick et al., *J. Bone Joint Surg.* 69A, 442 (1987)], respectively. However, anticoagulants alone may not provide maximal tissue protection, since reperfusion injury was found to occur in defibrinated animals [Simpson et al., *J. Pharmacol. Exp. Ther.* 256, 780–6 (1991)]. Furthermore, it is interesting to note that epigastric flaps survived better by the combined use of anticoagulants (heparin and urokinase) with superoxide dismutase and catalase [Maeda et al., *J. Reconstr. Microsurg.* 7, 233–243 (1991)]. All these results taken together suggest that ischemia/reperfusion injury involves a complex interplay of many biochemical, humoral and cellular pathways, all of which may contribute to the eventual tissue injury. Compounds that inhibit various points of the pathways may lead to different degrees of modulation of the complex cascade of events that lead to tissue injury and necrosis.

Other recently proposed drug treatments for ameliorating tissue damage from ischemia and reperfusion include the use of a non-anticoagulant heparin as described in PCT WO 94/08595, published Apr. 28, 1994, and detoxified endotoxins monophosphoryl lipid A or 3-deacylated monophospholipid A as disclosed in U.S. Pat. No. 5,286,718, dated Feb. 15, 1994.

It is known that plasma contains a multivalent Kunitz-type inhibitor of coagulation, referred to herein as tissue factor pathway inhibitor (TFPI). This name has been accepted by the International Society on Thrombosis and Hemostasis, Jun. 30, 1991, Amsterdam. TFPI was previously known as lipoprotein-associated coagulation inhibitor (LACI). TFPI was first purified from a human hepatoma cell, Hep G2, as described by Broze and Miletich, *Proc. Natl. Acad. Sci. USA* 84, 1886–1890 (1987), and subsequently from human plasma as reported by Novotny et al., *J. Biol. Chem.* 264, 18832–18837 (1989); and Chang liver and S. K. hepatoma cells as disclosed by Wun et al., *J. Biol. Chem.* 265, 16096–16101 (1990). TFPI cDNA have been isolated from placental and endothelial cDNA libraries as described by Wun et al., *J. Biol. Chem.* 263, 6001–6004 (1988); and Girard et al., *Thromb. Res.* 55, 37–50 (1989). The primary amino acid sequence of TFPI, deduced from the cDNA sequence, shows that TFPI contains a highly negatively charged amino-terminus, three tandem Kunitz-type inhibitory domains, and a highly positively charged carboxyl terminus. The first Kunitz domain of TFPI is needed for the inhibition of the factor $VII_a$/tissue factor complex, and the second Kunitz domain of TFPI is responsible for the inhibition of factor $X_a$ according to Girard et al., *Nature* 328, 518–520 (1989), while the function of the third Kunitz domain remains unknown. See also U.S. Pat. No. 5,106,833. TFPI is believed to function in vivo to limit the initiation of coagulation by forming an inert, quaternary factor $X_a$: TFPI: factor $VII_a$: tissue factor complex. Further background information on TFPI can be had by reference to the recent reviews by Rapaport, *Blood* 73, 359–365 (1989); and Broze et al., *Biochemistry* 29, 7539–7546 (1990).

Recombinant TFPI has been expressed as a glycosylated protein using mammalian cell hosts including mouse C127 cells as disclosed by Day et al., *Blood* 76, 1538–1545 (1990), baby hamster kidney cells as reported by Pedersen et al., *J. Biol. Chem.* 263, 16786–16793 (1990), Chinese hamster ovary cells and human SK hepatoma cells. The C127 TFPI has been used in animal studies and was shown to be effective in the inhibition of tissue factor-induced intravascular coagulation in rabbits according to Day et al., supra, and in the prevention of arterial reocclusion after thrombolysis in dogs as described by Haskel et al., *Circulation* 84, 821–827 (1991).

Recombinant TFPI also has been expressed as a non-glycosylated protein using *E. coli* host cells and obtaining a highly active TFPI by in vitro folding of the protein as described in U.S. Pat. No. 5,212,091, the disclosure of which is incorporated by reference herein. See also Wun et al., *Thromb. Hemostas.* 68, 54–59 (1992).

The cloning of the TFPI cDNA which encodes the 276-amino acid residue protein of TFPI is further described in Wun et al., U. S. Pat. No. 4,966,852, the disclosure of which is incorporated by reference herein.

Recently, TFPI obtained through recombinant DNA clones expressed in *E. coli* as disclosed in U.S. Pat. No. 5,212,091, has been described as useful for reducing the thrombo-genicity of microvascular anastomoses. See U.S. Pat. No. 5,276,015, the disclosure of which is incorporated herein by reference.

The use of TFPI for treatment of sepsis or septic shock and sepsis-associated disorders is described in recently published patent applications PCT WO 93/24143 and PCT WO 93/25230.

BRIEF DESCRIPTION OF THE INVENTION

In accordance with the present invention, a novel method is provided for inhibiting tissue ischemia and reperfusion injury in all its forms in a warm-blooded mammal manifesting a bodily injury subject to interval tissue ischemia. The method comprises administering to said mammal, by local, regional or systemic perfusion to the site of a bodily injury subject to interval tissue ischemia, a small but effective amount of tissue factor pathway inhibitor (TFPI) sufficient to reduce the extent of tissue ischemia and reperfusion injury.

The invention is illustrated in particular hereinbelow by the regional perfusion of the TFPI (a) to a rabbit ear ischemia/reperfusion model; (b) to a rabbit model of spinal cord ischemia resembling that which may occur clinically after cross-clamping of the aorta during aneurysm repair, and (c) to a model of ischemia/reperfusion injury in a rabbit rectus femoris muscle to demonstrate skeletal muscle survival.

Many factors and mechanisms contribute to the ultimate tissue damage after a period of partial or total ischemia followed by reperfusion. As in the case of reperfusion after a stroke, myocardial infarction, angioplasty, replantation or free-flap tissue transfer, the period of reperfusion can be complicated by further tissue injury caused by thrombosis, inflammation or tissue swelling and edema. There is, however, a time limit beyond which effective tissue reperfusion (no reflow) does not occur. The estimated time limits of development of the no-reflow phenomenon in experimental skin-free flaps is 12 (twelve) hours, while in tissues such as myocardium, cellular tissue changes are seen within minutes and no reflow can develop within one hour [May et al., *Plast. Reconstr. Surg.* 76, 737 (1978)]. Identification of an agent such as TFPI as described herein that can safely limit the extent of tissue injury in the clinical setting of crush injury, amputation, organ transplantation, cerebral vascular diseases (e.g. stroke), ischemic heart diseases (e.g. myocardial infarction) and peripheral vascular diseases, would have great clinical utility.

The length of ischemia is one of the more critical factors determining the outcome of ischemia/reperfusion. The rabbit ear ischemia/reperfusion model described herein required an ischemia time of approximately 20 (twenty) hours to give rise to necrosis of the ear after reperfusion. Other investigators have reported 8–12 hours of ischemia time to produce necrosis in the presence of blood [Zarem et al., *Plast. Reconstr. Surg.* 82, 865–871 (1987)]. In the present model the effect of stagnant blood [Rosen et al., *Surg. Forum* 35, 601 (1984)] has been eliminated. Therefore, the ischemia time needed to produce necrosis was higher than what has been reported previously.

In view of the substantial evidence that suggests a link between coagulation and inflammation [Esmon et al., *Thromb. Haemost.* 66, 160–165 (1991)], the effect of TFPI in the rabbit ear ischemia/reperfusion model was compared with the effect of the conventional anti-coagulant hirudin (a specific thrombin inhibitor) and a saline control in the same animal model. Surprisingly, while hirudin treatment aggravated the injury leading to hemorrhagic necrosis, TFPI treatment greatly enhanced the survival of the ears. The reasons for this unexpected difference in these two anti-coagulants in their effect on ischemia/reperfusion injury are not clear but may be related to their different mechanisms of action. Hirudin is a highly potent inhibitor of thrombin. It exerts a sustained antithrombotic activity long after its plasma clearance because of its ability to inhibit thrombus extension caused by both the fluid phase- and fibrin-bound thrombin [Agnelli et al., *Blood* 80, 960–965, 1992)]. In contrast, TFPI does not inhibit thrombin directly. TFPI inhibits the tissue factor/factor VIIa-induced activation of factor X and IX in a feedback, factor Xa-dependent manner. Thus, a small amount of thrombin is generated before the coagulation cascade is shut off [Broze et al., *Biochemistry* 29, 7539–7546 (1990)]. Thrombin has a number of actions, including:

the formation of fibrin;

the aggregation of platelets [Berndt and Phillips, in *Platelets in Biology and Pathology*, (E. D. Gordon, ed.) Elsevier/North Holland Biomedical Press, Amsterdam, 1981, pp. 43–74];

the adherence of neutrophils to vessel wall by an endothelium-dependent mechanism [Zimmerman et al., *Ann. N.Y. Acad. Sci.* 485, 349–368 (1986)];

the chemotaxis of monocytes [Bar-Shavit et al., *J. Cell Biol.* 96, 282–285 (1983)];

the mitogenic proliferation of lymphocytes, fibroblasts, and vascular smooth muscle cells [Carney et al., *Sem. Thromb. Hemost.* 18, 91–103 (1992)]; and the modulation of vascular functions [Blusa, *Sem. Thromb. Hemost* 18, 296–304 (1992)].

It has been suggested that thrombin plays a critical role in inflammation [Drake and Issekutz, *Sem. Thromb. Hemost.* 18, 333–340 (1992)] as well as in wound healing and tissue repair [Stiernberg et al., *Thromb. Haemost.* 70, 158–162 (1993)]. Thus, it is possible that the conventional anticoagulant, hirudin, may aggravate the hemorrhagic necrosis by excessive inhibition of thrombin which is requisite for tissue repair after injury. In contrast, TFPI may exert a beneficial anti-inflammatory effect in ischemia/reperfusion injury by limiting excessive generation of thrombin, but allowing a localized generation of a small amount of thrombin in the injured site for tissue repair. However, the inventors are not bound by scientific theory and, therefore, the present invention is not limited to the foregoing scientific explanation and alternative explanations are not excluded. For example, TFPI may exert its action through other yet unidentified targets in the ischemia/reperfusion injury pathways.

Spinal cord injury is the most serious complication of spinal column trauma and also of operations on the aorta for treatment of thoracic and thoracoabdominal aneurysms [Kouchoukos, *J. Thorac. Cardiovasc. Surg.* 99:659–664, (1990)]. The spinal cord is the organ most sensitive to ischemia during cross-clamping of the aorta. The resulting injury can produce paraparesis or paraplegia. Spinal cord ischemia and paraplegia develop in approximately eleven percent (11%) of patients undergoing elective descending thoracic and thoracoabdominal aneurysm repair and nearly forty percent (40%) undergoing emergent repairs [Crawford, *J. Vas. Surg.* 3:389–402, (1986)]. Several investigators have observed a progressive worsening of post-traumatic ischemia during the first few hours after injury, indicating that some damage might be preventable if treated early [Tator and Fehlings, *J. Neurosurg.*, 75:15–26, (1991)]. The ability to minimize nerve damage developing from ischemia/reperfusion is currently lacking. Therefore, an animal model of spinal cord ischemia resembling that which may occur clinically after cross-clamping of the aorta during aneurysm repair was also employed herein to illustrate the desirable effect of TFPI in limiting reperfusion injury in the spinal cord.

The tissue injury that occurs after a period of total ischemia and subsequent revascularization (ischemia/reperfusion injury) has several proposed mechanisms that often lead to partial or complete tissue necrosis. The extent of injury depends upon the length of time and degree of ischemia as well as the tissues affected. Although studies have been conducted on skeletal muscle, these complex responses are poorly understood. Tissue reperfusion injury is seen clinically in its full extent as the no-reflow phenomenon where the large vessels to an organ or tissue are providing blood but the microcirculation does not accept the blood for nutritive circulation. The microvascular circulation appears to play a crucial role in the events which lead to the inability of tissue to have a restored circulation. Attempts to protect the microcirculation or prolong the time which ischemia can be tolerated could limit the impact of reperfusion injury on skeletal muscle tissue. Therefore, a model was utilized herein to show the effect of TFPI on ischemia/reperfusion injury in the rabbit rectus femoris muscle. This muscle is perfused by a single artery and vein and thus is an ideal model for studying ischemia/reperfusion injury in skeletal muscle. This example illustrates the effect of TFPI in protecting against ischemia/reperfusion injury of skeletal muscle.

It will be appreciated that although the method of the invention is illustrated in particular hereinbelow with the rabbit species, it is also useful for other warm blooded mammals, e.g., humans, in an analogous manner.

As defined herein, TFPI can be either glycosylated or non-glycosylated.

DETAILED DESCRIPTION OF THE INVENTION

While the specification concludes with claims particularly pointing out and distinctly claiming the subject matter which is regarded as forming the present invention, it is believed that the invention will be better understood from the following detailed description of preferred embodiments taken in conjunction with the accompanying drawings in which:

BRIEF DESCRIPTION OF THE DRAWINGS

FIG. 1 is a bar graph that shows ear survival in a rabbit ear ischemia/reperfusion model in which the rabbits were treated with TFPI in a phosphate-buffered saline (PBS) solution, pH 7.4, as vehicle compared to ear edema of rabbits treated with hirudin in the same PBS vehicle or to rabbits treated only with the PBS vehicle as a control. Ears surviving (both total and partial survival) and ears showing total necrosis compared as a percent of ears treated are shown at three post-operative (post reperfusion) time periods, namely Day 5, Day 7, and Day 10. Hirudin-treated ears showed no improvement compared to control. TFPI ears were significantly better than either hirudin (p<0.029) at Day 10 and control (p<0.00000035 and p<0.00000027) at Day 7 and Day 10, respectively.

FIG. 2A shows the six hour histologic sections in the TFPI treated specimens compared to FIG. 2B which shows the six hour histologic sections in the control specimens. This comparison reveals fewer marginating neutrophils in the TFPI treated specimens versus control.

FIG. 3A shows the twenty four hour histologic sections in the TFPI treated specimens compared to FIG. 3B which shows the twenty four hour histologic sections in the control specimens. This comparison reveals increased number of neutrophils in control ears which reflects greater inflammatory response and shows higher numbers of neutrophils per field in the surrounding perivascular tissue of control versus TFPI treated specimens.

FIG. 4 is a bar graph which shows the effect of TFPI on limiting spinal cord injury in a rabbit model of spinal cord ischemia. As seen in Table I below, 8 of 17 (47%) control rabbits are completely paralyzed or grade zero (0); 3 (17.6%) had a grade 1; 1 (5.9%) had a grade 2; 1 (5.9%) had a grade 3; and only 4 (23.5%) had a grade 4. None of 20 TFPI-treated rabbits had grade 0; 2 (10%) had a grade 1; 3 (15%) had a grade 2; 6 (30%) had a grade 3; and 9 (45%) had a grade 4, which is complete recovery. Very little difference exists between animals graded 3 and 4, which are both considered as recovery of function. Animals graded zero (0) and 1 are considered lack of recovery. The TFPI-treated animals exhibited 75% recovery in comparison to about 30% recovery in control animals.

Figure 2A:
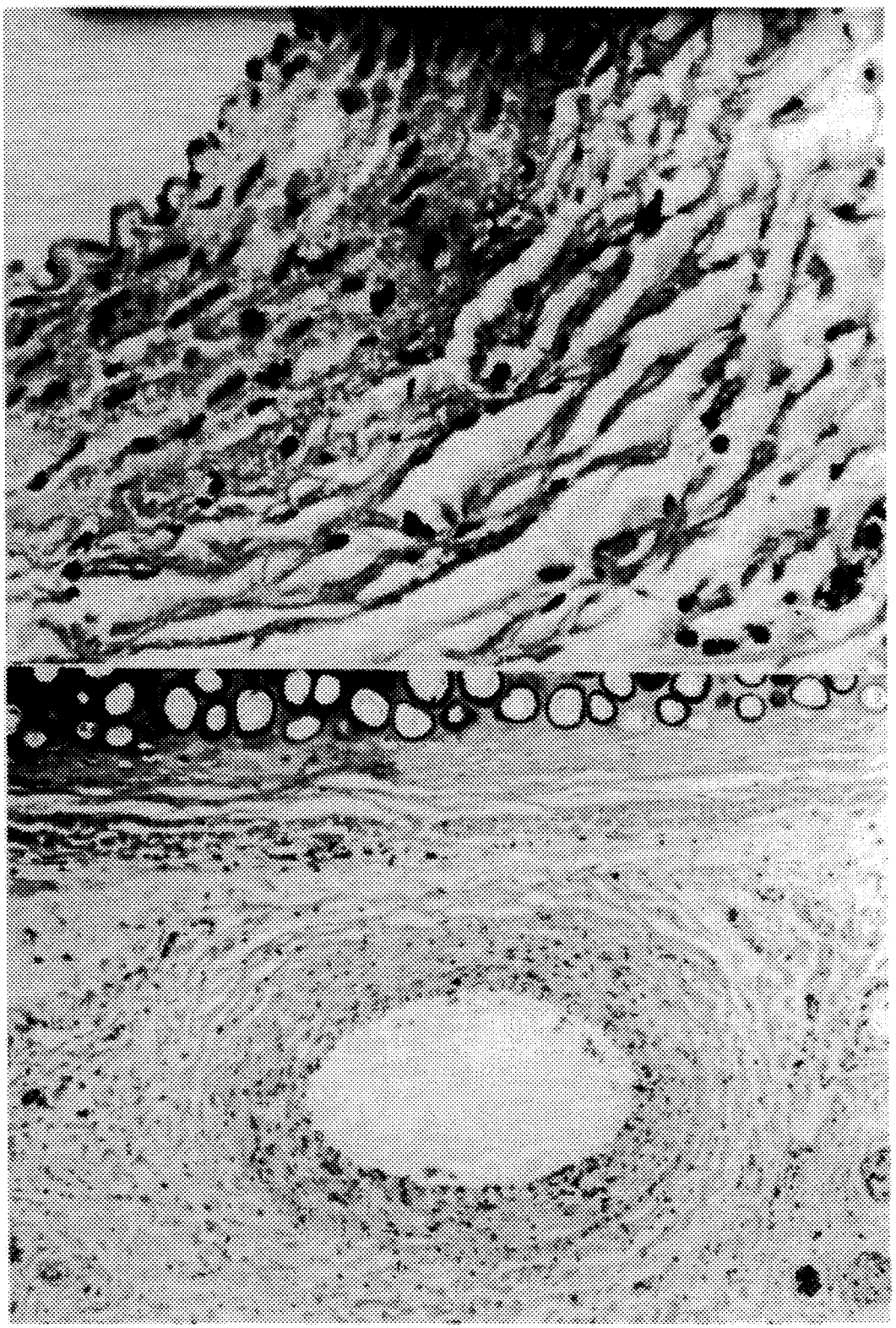
FIGS. 2A, 2B, 3A and 3B show histologic sections of the rabbit ears subjected to the rabbit ear ischemia/reperfusion model of FIG. 1 for animals treated with either TFPI or the PBS control vehicle in which the upper panels are shown at 138×magnification whereas the lower panels are shown at 555×magnification.

This resulted in a mean score of 1.412 and a standard deviation of 1.700 for the control group while the TFPI-treated group had a mean score of 3.100 and a standard deviation of 1.021. A student's t-test was performed to test the significance of their means and the resulting p-value was 0.0014. Thus, the TFPI-treated group had a statistically significant better recovery than the control group.

FIG. 5 is a bar graph which shows the effect of TFPI on muscle survival in a rabbit rectus femoris muscle model. Rabbits were divided into four groups: Sham (no ischemia, no treatment, n=7); Control (ischemia, no treatment, n=9); PBS (ischemia, PBS treatment, n=7); and TFPI (ischemia, TFPI treatment, n=8).

The area of necrosis was traced on paraffin paper and then digitized. This was compared with the total area of the muscle to determine percent muscle viability. As seen in Table II, below, animals that received sham surgery had a 95.2% survival with the mean of ±1.6; control animals had a 42.6% survival with the mean of ±7.2; PBS-treated animals had a 49.0% survival with the mean of ±7.7. In contrast, TFPI-treated animals had a 78.1% survival with a mean of ±14.0, which is much higher than the control and the PBS-treated animals. Statistical significance was found in comparing TFPI versus sham, control and PBS-treated animals.

In order to illustrate the invention in greater detail, the following illustrative Examples using a rabbit ear ischemia/reperfusion model (EXAMPLE I); a rabbit model of spinal cord ischemia (EXAMPLE II); and a model of rabbit rectus femoris muscle (EXAMPLE III), were carried out. It will be appreciated, however, that the invention is not limited to this exemplary work nor to the specific details set forth in these Examples.

The TFPI used in the Examples was obtained through recombinant DNA clones expressed in *E. coli*. It is a 277-amino acid protein consisting of the 276 residue sequence described by Wun et al., *J. Biol. Chem.* 263, 6001–6004, (1988), and in U.S. Pat. No. 4,966,852, with an additional alanine residue inserted at the N-terminus as described in U. S. Pat. No. 5,212,091. The hirudin was purchased from American Diagnostica, Inc. (Greenwich, Conn.).

EXAMPLE I

Materials and Methods

Sixty-Two (62) New Zealand white rabbits weighing 2.5–3.5 kg each were anesthetized with a combination of xylazine (7 mg/kg) and ketamine (35–50 mg/kg). One ear of each animal was shaved, prepped with betadine and draped. A circumferential skin incision was made around the ear, the small subcutaneous vessels and the marginal arteries were carefully cauterized and the perichondrium was then exposed for 5 mm on either side of the skin incision. After carefully isolating the central neurovascular pedicle of the ear, the cartilage was divided at the base of the ear and then was reapproximated to provide a stable ear construct. Using a dissecting microscope, after examining the vessels to be sure they were free from injury, they were stripped of the surrounding tissues including the adventitia. The accompanying nerve was transsected. Subsequently, a small caliber microclip was placed on the artery to effect circulatory arrest. A small arteriotomy was made and a PE-10 polyethylene catheter was placed into the artery. A total of 3 cc of either TFPI, hirudin or phosphate-buffered saline (PBS) control was regionally perfused with the excess fluids being flushed into the systemic circulation. Immediately following regional infusion a second small caliber microclip was placed on the vein to insure total circulatory arrest. Animals were divided into three groups: Group 1 received TFPI 20 µg/ml, Group 2 received Hirudin 100 anti-thrombin units (ATU)/ml, and Group 3 received phosphate-buffered saline, pH 7.4, which was the vehicle for the TFPI and Hirudin.

The skin was approximated with 4-0 nylon sutures closing the vessels with the clamps under the skin. A total ischemic interval of 20 hours was achieved while the animals were back in their cages being given food and water ad libitum.

After the 20-hour ischemic interval, all animals were reanesthetized, the wound was opened, and a second regional perfusion was administered through an intra-arterial catheter, after removing the venous clamp. The arteriotomy site was then closed under the operating microscope using 10-0 nylon microsuture. The microclamp was removed from the artery, establishing reperfusion, the skin closed and the animals were housed in a thermally controlled area maintained between 22°–24° C. The animals were observed daily. Ear tissue survival was monitored daily for tissue necrosis until post-operative day 10. Necrosis was demonstrated as a dull pale area with coagulation necrosis and eschar formation. Ears were recorded as total survival, partial survival or complete necrosis. For statistical analysis, the p value was calculated by assigning 1 to complete survival, 0.5 to partially necrosed ears, and 0 to completely necrosed ears using a T-test.

Using the same protocol as above, another 18 rabbits were divided into two groups to receive TFPI or phosphate-buffered saline (PBS) as control for histological evaluation. In each group, animals were sacrificed at one, six and 24 hours post-reperfusion and their ears were harvested immediately and processed for Hematoxylin and Eosin staining.

RESULTS

Daily Visual Observation and Ear Survival

In a preliminary test, in order to establish the ischemic time that resulted in the necrosis of the ear after reperfusion, various ischemic intervals were tried (10, 16, 18 and 20 hours). It was found that 10, 16 or 18 hours of ischemia did not result in necrosis of the ear for at least 10 days in the control ears treated with PBS, although signs of inflammation (swelling, above-normal temperature of the ear) were observed. However, when the ischemia time was prolonged to 20 hours, the ears appeared to be inflamed in the first five (5) days and became necrotic between 5–10 days post operative. Therefore, a 20-hour ischemia time was chosen for comparison of the effects of TFPI, hirudin, and PBS control solution on the ischemia reperfusion injury. In the three groups above, all animals survived the first 5 days post reperfusion. However, daily ear volume measurement and visual observation of the ears suggested different responses in these three groups. The TFPI-treated group generally showed less ear swelling than the controls, but no statistical significance was observed in this aspect.

The hirudin-treated group, in contrast, appeared hyperemic and hemorrhagic, which was not observed in the control and TFPI-treated animals. By Day 7, most of the ears in the TFPI-treated group survived, while the control and hirudin-treated ears had higher incidences of partial and/or total necrosis (FIG. 1). At Day 10, two (2) animals in the TFPI-treated group were sacrificed because of infection, four (4) ears underwent total necrosis; three (3) were partially necrosed, while the remaining sixteen (16) completely recovered. In contrast, in the hirudin group, only one had completely recovered, one partially necrosed, and four (4) totally necrosed. In the thirty-one (31) saline-treated ears, three (3) completely recovered; seven (7) were partially necrosed; and twenty-one (21) underwent total necrosis (FIG. 1). These results show that, surprisingly, TFPI treatment inhibits the long term reperfusion injury, while hirudin treatment promotes hemorrhagic necrosis.

Histology

Figure 2B:
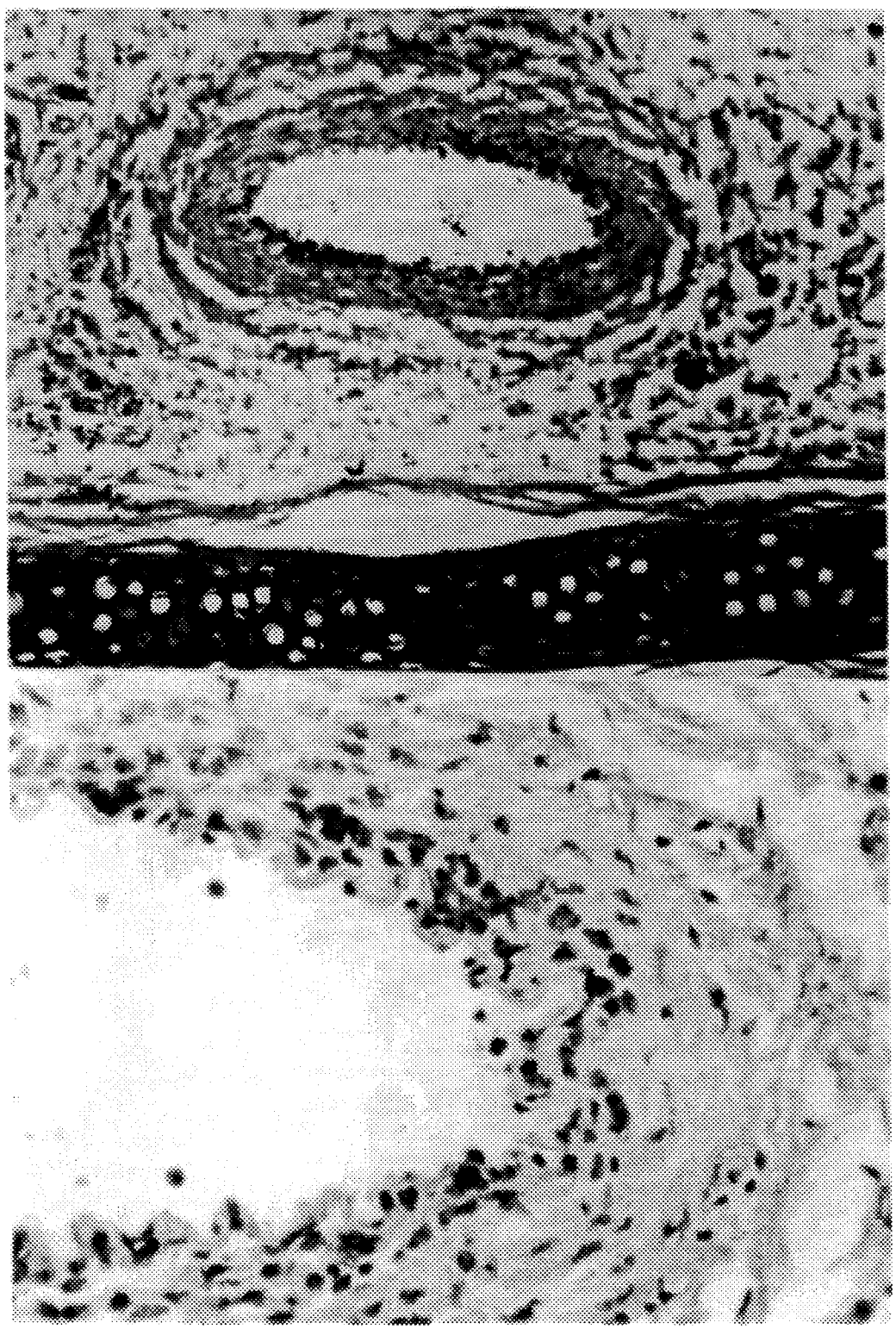
Figure 3A:
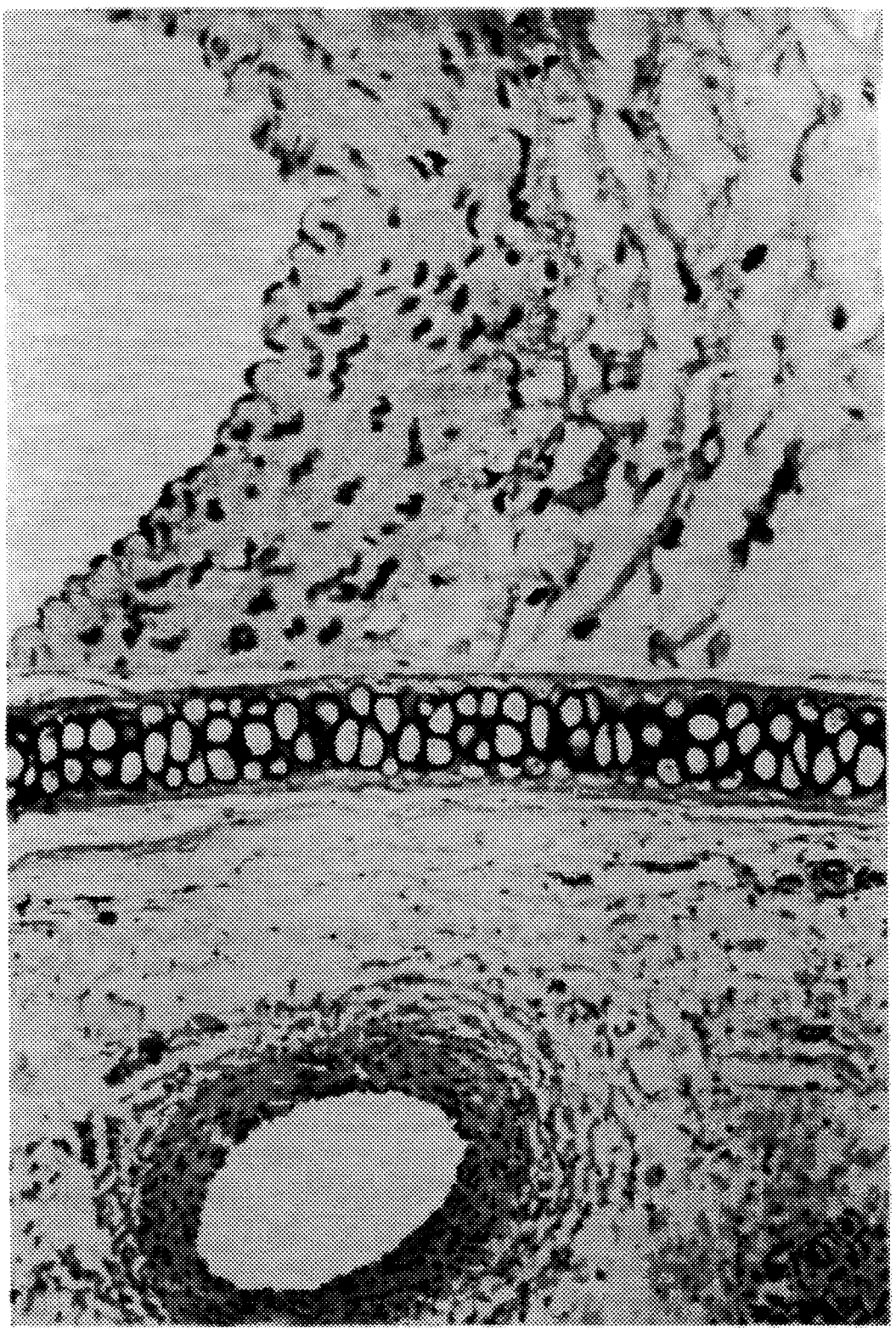
Figure 3B:
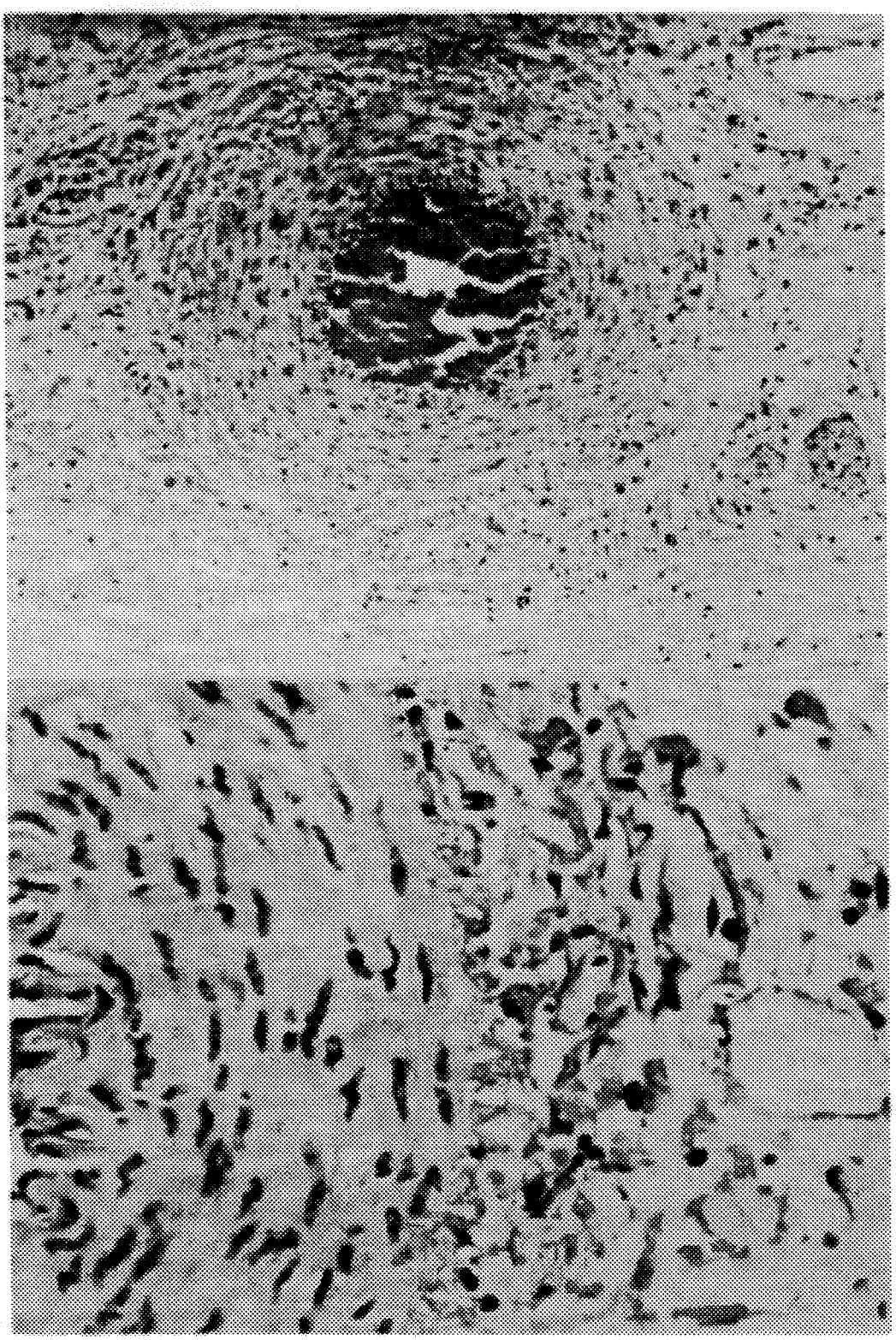

An identical ischemia/reperfusion procedure as above was applied to two separate groups of animals by treating the ear with PBS or TFPI and the tissues harvested at various times after reperfusion for histological comparison. At six hours after the onset of reperfusion, a large number of neutrophils were seen to have penetrated the vascular endothelium and migrated deeper into the vessel wall in the PBS-treated ears (FIG. 2B). Many of these neutrophils appeared to be degranulating. In comparison, fewer numbers of neutrophils were seen in the TFPI-treated ear vessels (FIG. 2A). At 24 hours after reperfusion, the neutrophils were seen to have migrated into the adventitia in less numbers in the TFPI-treated ears (FIG. 3A) than the control (FIG. 3B). It should. be understood that the invention is not limited to neutrophil penetration as observed in this Example or other such histological conclusions.

EXAMPLE II

MATERIALS AND METHODS:

A highly developed rabbit model of spinal cord ischemia was established by Zivin and DeGirolami, *Stroke* 11:200–202, (1980). This model has been applied subsequently by numerous authors to study events during cord ischemia [Jacobs, *Stroke*, 18:741–750, (1987); Jacobs, *Stroke* 23:367–373, (1992); J. Robertson, *J. Neurosurg.* 64:633–642, (1986)]. The rabbit has now become the model of choice because it yields more consistent results [DeGirolami, *J. Neuropath., Exp. Neurol* 41(2):129–149, (1982)]. In assessing this model, Robertson et al have stated: "the rabbit spinal cord is a reliable model for systematically and rapidly screening agents that might have protective effects during ischemia". [Robertson, *J. Neurosurg.*, 64:633–642, (1986)].

New Zealand White rabbits (2.5–3.0 kg) were sedated with ketamine (25 mg/kg) administered intramuscularly. The anesthetic effect was prolonged using oxygen and isofluorane. After induction of anesthesia, rabbits were intubated and attached to a ventilator. The right ear, neck, abdomen and both groins were shaved, cleansed with iodophor and draped in sterile fashion. An IV catheter was placed in the central vein of the right ear through which normal saline was infused. The right carotid and femoral arteries were cannulated for infusion of either buffered saline containing TFPI (20 µg/ml) or buffered saline (control). Both the TFPI and buffered saline were kept in an ice water bath. Heparinized saline was used to flush the catheters and body temperature closely monitored and euthermia maintained. Blood samples (~0. 5 ml) were drawn from the right carotid artery catheter to measure the animal's blood gas and electrolyte levels. When the $Po_2$ and $pCO_2$ stabilized, $Po_2$ between 100–120 mm Hg and the hematocrit level is between 30–33%, the abdomen was opened.

The aorta was approached through an abdominal midline incision. The small and large bowels were retracted to the right side and draped with a warmsaline soaked towel, exposing the abdominal aorta. The aorta and its branches were meticulously dissected immediately distal to the left renal artery where it was clamped, thereby disrupting blood supply to the lumbar spinal cord. Twenty milliliters of either buffered saline of buffer saline plus TFPI (20 µg/ml) was infused twice under pressure equal to the pre-ischemic pressure reading from the femoral transducer. The infusions occurred at the onset of ischemia and just prior to reperfusion. After an ischemic interval of twenty minutes, the vascular clamp was removed establishing reperfusion. The bowel was placed in the abdominal cavity and the abdominal wall closed with 4-0 nylon suture in separate layers. The catheters were removed and the arteries ligated to prevent hemorrhage. The skin was closed with 4-0 nylon.

EVALUATION:

Neurologic:

At 24 hours post reperfusion, neurological status was graded by assessment of hind limb neurologic function according to the modified Tarlov criteria, as follows (Jacobs, supra):

Grade 0: no voluntary function

Grade 1: movement of joints perceptible

Grade 2: active movement of joints but unable to stand

Grade 3: able to stand but unable to walk

Grade 4: complete recovery.

RESULTS:

Neurologic results are summarized in Table I:

TABLE I

|       | GROUP   |      |
| ----- | ------- | ---- |
| GRADE | CONTROL | TFPI |
| 4     | 4       | 9    |
| 3     | 1       | 6    |
| 2     | 1       | 3    |
| 1     | 3       | 2    |
| 0     | 8       | 0    |

The difference in mean grade between control and TFPI groups was highly significant using student's T-test (p<0.0014).

EXAMPLE III

MATERIALS AND METHODS:

Rabbits were anesthetized with xylazine (7 mg/kg) ketamine (25 mg/kg) and acetylpromazine (2 mg/kg). After induction of anesthesia, a skin incision was made from the inguinal ligament to the knee along the medial thigh. Using an electric cautery for meticulous hemostasis and blunt dissection, the lateral margins of the rectus femoris were dissected free except for a marginal artery and vein through which either TFPI or phosphate-buffered saline (vehicle control) was infused. In tests where no drug was infused, the marginal artery and vein were cauterized. The distal portion of its tendinous insertion was transsected. Subsequently, the tendons were transsected proximally. The marginal artery was first tied and then cannulated for infusion of either drug. A microvascular clamp was placed across the rectus femoris central artery and vein thus beginning the ischemic period. Immediately following the onset of ischemia a total of 3 cc of either TFPI 20 μg/ml or phosphate-buffered saline (PBS) alone was regionally perfused with the excess fluids being flushed into the systemic circulation. Immediately following regional infusion a second small caliber microclip was placed on the marginal vein to ensure total circulatory arrest, and was removed just prior to the second infusion. The muscle flap was then placed and secured in its original position with a few sutures and the skin sutured closed. After three and one-half hours of ischemia, the animal was re-anesthetized and the skin opened. A second infusion of either TFPI or phosphate-buffered saline was given through the marginal artery and the vascular clamps removed and wound reclosed. Sham surgeries were performed on the opposite muscle in the same manner except that the muscle was not subjected to a period of ischemia.

After 24-hours post reperfusion, the animals were again anesthetized and the rectus femoris removed. A slice of the muscle was removed for histology and measurement of wet and dry weights to determine the degree of edema. The rest of the muscle was sliced and incubated in a phosphate-buffered solution of Nitro blue tetrazolium (NBT) (8 mg/ml). The area of necrosis was traced on paraffin paper and then digitized. This was compared with the total area of the muscle to determine percent muscle viability.

RESULTS:
Rabbits were divided into four groups:
control (no drug infusion, n=9)
sham (no ischemic period, n=7)
TFPI-treated animals (n=8)
PBS-treated animals or vehicle control (n=7).
The results are set forth in Table II:

TABLE II

| GROUP | PERCENT MUSCLE SURVIVAL MEAN ± SEM |
| --- | --- |
| CONTROL | 42.6 ± 7.2% |
| SHAM | 95.2 ± 1.6% |
| TFPI | 78.1 ± 14.0% |
| PBS | 49.0 ± 7.7% |

Statistical significance was determined using a student's T-test for comparing mans. Results are set forth in Table III:

TABLE III

| GROUP | P-VALUE |
| --- | --- |
| CONTROL vs SHAM | 2.66 × 10$^{-11}$* |
| TFPI vs CONTROL | 7.22 × 10.$^{-6}$* |
| TFPI vs PBS | .0003* |
| TFPI vs SHAM | .0071* |
| PBS vs CONTROL | .1088 |

*-indicates statistical significance found

Although the invention has been described in detail herein with respect to reducing the extent of tissue ischemia/reperfusion injury in an ear ischemia/reperfusion setting, in spinal cord and skeletal muscle ischemia, the invention is also useful for other clinical settings involving bodily injury subject to interval tissue ischemia, e.g. coronary vascular diseases such as acute myocardial infarction, coronary bypass, angioplasty, cerebral vascular diseases such as stroke, peripheral vascular diseases, carotid bypass surgery, microsurgery of thromboembolic disease, cross-clamp aorta, lung transplantation, pulmonary thromboembolism, re-expansion pulmonary edema, aortic-femoral bypass surgery, femoral popliteal bypass, aortic aneurysm, hypovolemic shock, major trauma, tourniquet, other transplants and free-flap transfer.

Administration of the TFPI by local, regional or systemic perfusion is preferably carried out by administration of the TFPI from admixture with a physiologically acceptable vehicle or carrier, e.g., normal saline or buffered saline such as phosphate-buffered saline or other such pharmaceutically acceptable buffers, e.g., HEPES. The TFPI can also be administered in powder, salve or ointment form in conventional pharmaceutically acceptable vehicles. Such conventional vehicles are well known to the person skilled in the art, as can be seen by reference to numerous texts and treatises in the field of drug administration, e.g., *Remington's Pharmaceutical Sciences*, ed. Arthur Osol, 16 ed., 1980, Mack Publishing Co., Easton, Pa. The amount of TFPI administered to the site of the injury or systemically administered, can be a small amount depending in part on the degree or severity of the injury. The amount to be administered must be an effective amount, that is, an amount which is medically beneficial but does not present toxic effects which overweigh the advantages which accompany its use. It is expected that the adult human dose administered systemically would range upward from about 0.1 mg of the active drug and preferably from about 1 to about 100 mg/Kg of body weight. Doses of TFPI of from about 1 μg/ml to about 1000 μg/ml in pharmaceutically acceptable solution of from about 1 ml to about 100 ml are suitable.

Various other examples will be apparent to the person skilled in the art after reading the present disclosure without departing from the spirit and scope of the invention. It is intended that all such other examples be included within the scope of the appended claims.

What is claimed is:

1. A method for reducing tissue ischemia and reperfusion injury in a mammal caused by ischemia and subsequent reperfusion of blood flow into said tissue, which method comprises perfusing into said tissue an effective amount of tissue factor pathway inhibitor (TFPI).

2. The method of claim 1 wherein said TFPI is administered prior to total ischemia of said tissue.

3. The method of claim 1 wherein said TFPI is administered prior to reperfusion of blood flow into said tissue.

4. The method of claim 1 wherein said TFPI is administered prior to subsequent reperfusion of blood flow into said tissue.

5. The method of claim 1 wherein said TFPI is administered by systemic perfusion.

6. The method of claim 1 wherein TFPI is administered by regional perfusion.

7. The method of claim 1 wherein TFPI is administered by local perfusion.

8. The method of claim 1 wherein TFPI is carried by a phsiologically acceptable vehicle.

9. The method of claim 8 wherein TFPI is from about 1 μg/ml to about 1000 μg/ml in said physiologically acceptable vehicle.

10. The method of claim 1 wherein TFPI is (ala$^{-1}$)–TFPI (1–277) or native TFPI (1–276).

11. The method of claim 1 wherein TFPI is the first and second Kunitz domain of said TFPI.

12. The method of claim 11 futher comprising an additional alanine at the N-terminus of said TFPI.

13. The method of claim 4 wherein TFPI is the first or second Kunitz domain of said TFPI.

* * * * *